United States Patent [19]

Morita et al.

[11] 4,181,803
[45] Jan. 1, 1980

[54] PROPIOPHENONE DERIVATIVES AND PREPARATION THEREOF

[75] Inventors: Eiichi Morita; Takeo Kanai, both of Honjou, Japan

[73] Assignee: Eisai Co., Ltd., Tokyo, Japan

[21] Appl. No.: 666,073

[22] Filed: Mar. 11, 1976

Related U.S. Application Data

[63] Continuation of Ser. No. 530,499, Dec. 6, 1974, abandoned.

[30] Foreign Application Priority Data

Dec. 14, 1973 [JP] Japan .................. 48-138808

[51] Int. Cl.² ........................................... C07D 295/10
[52] U.S. Cl. ..................................... 546/237; 424/267
[58] Field of Search ................................. 546/237

[56] References Cited

U.S. PATENT DOCUMENTS 2,771,391  11/1956  Bockstahler .................. 260/293.8

FOREIGN PATENT DOCUMENTS 1916055  10/1969  Fed. Rep. of Germany .
40-20390  9/1965  Japan .

OTHER PUBLICATIONS

Ueda et al., Chemical Abstracts, vol. 56 (1962) 12863a.
Name Reactions in Organic Chemistry (1954) Surrey, pp. 118–120.
Porszasz et al., Chemical Abstracts, vol. 55 (1961) 13637a.
Kato et al., Jour. Pharmacol. Exptl. Therapeutics, vol. 149, No. 1 (1965), pp. 131–137.

*Primary Examiner*—Norma S. Milestone
*Attorney, Agent, or Firm*—Wenderoth, Lind & Ponack

[57] ABSTRACT

New propiophenone derivatives prepared by the reaction of propiophenone, formaldehyde and piperidine, as well as pharmacologically acceptable acid-addition salts thereof are provided, which possess improved pharmacological activities such as anti-tramorine and anti-nicotine activities superior to those of the known analoguous compound. The new compounds are useful for the therapeutic treatment of human patient suffering from pathological muscular contracture, spastic paralysis due to cerebral apoplexy, spinal and cerebral palsies and the like.

4 Claims, No Drawings

PROPIOPHENONE DERIVATIVES AND PREPARATION THEREOF

This is a continuation, of application Ser. No. 530,499, filed Dec. 6, 1974 now abandoned.

This invention relates to the new amino-substituted propiophenone derivatives, that is, 4'-substituted 2-methyl-3-piperidino-propiophenones represented by the formula:

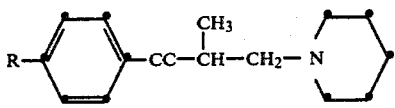

wherein R stands for a lower alkyl group having 2 to 3 carbon atoms, as well as pharmacologically acceptable acid-addition salts thereof, and a process for the preparation thereof.

It has been found that the new compounds of the present invention possess excellent anti-tremorine and anti-nicotine activities and thus useful for the therapeutic treatment of pathological muscular contracture, spastic paralysis due to cerebral apoplexy, spinal and cerebral palsies and the like. The compounds are also a prominant muscular relaxant for the stiffen muscle due to spinal polysynapse reflex-inhibiting action.

At present, 2,4'-dimethyl-3-piperidino-propiophenone hereafter called "Tolperisone" has been available in the market as the therapeutic agent clinically used for the treatment of spastic paralysis. The pharmacological activities of Tolperisone rely upon its spinal polysynapse reflex-inhibiting action and anti-tremorine and anti-nicotine activities.

As the result of thorough investigations effected by the present inventors for many years in order to discover another compound or compounds having therapeutic activities superior to those represented by Tolperisone, it has surprisingly been found that the new propiophenone derivatives represented by the formula:

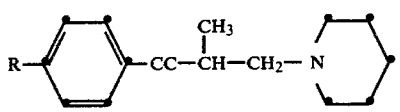

wherein R stands for a lower alkyl group having 2 to 3 carbon atoms, are superior to Tolperisone with respect to their pharmacological activities. The performance of the present invention indeed relies upon said particular observations.

Accordingly, an object of this invention is to provide the novel therapeutic agent represented by the abovementioned chemical formula (I) which is effective for the treatment of pathological muscular contracture, spastic paralysis due to cerebral apoplexy, spinal and cerebral palsies and the like.

Another object of the invention is to provide a novel muscular relaxant.

A further object of the invention is to provide a therapeutic agent having spinal polysynapse reflex-inhibitory activity, anti-tremorine and anti-nicotine activities and the like adaptable for the treatment of human patient suffering from pathological muscular contracture, spastic paralysis due to cerebral apoplexy, spinal and cerebral palsies and the like.

A still further object of the invention is to provide the novel propiophenone derivatives superior to Tolperisone with respect to the several pharmacological viewpoints.

A yet further object of the invention is to provide a process for the preparation of the abovementioned new therapeutic agent effective for the treatment of pathological muscular contracture, spastic paralysis due to cerebral apoplexy, spinal and cerebral palsies and the like.

It is also an object of the invention to provide a method for the therapeutic treatment of pathological muscular contracture, spastic paralysis due to cerebral apoplexy, spinal and cerebral palsies and the like.

The novel and useful propiophenone derivatives contemplated in the invention may be prepared by the process in which a ketonic compound, that is, 4'-substituted propiophenone represented by the formula:

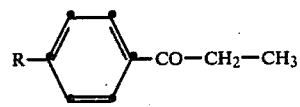

wherein R stands for a lower alkyl group having 2 to 3 carbon atoms, is caused to reaction with formaldehyde and piperidine.

Although the abovementioned chemical reaction can be effected by suitably warming a mixture of the abovementioned starting materials even in the absence of a reaction medium, it has been found that use of a suitable solvent is preferable and convenient for facilitating a finishing or working-up operation of the reaction product. Any conventional solvent may be employed for this purpose, and above all, lower alcohols such as methanol, ethanol, propanol and isopropanol are particularly mentioned therefor.

As to the formaldehyde as one of the reactants, there may preferably be employed a 30% aqueous solution of formaldehyde, that is, formalin, or paraformaldehyde.

The compounds of the formula (I) supra obtained by the process of the invention, if necessary, may be converted into their pharmacologically acceptable acid-addition salts by means of a conventional method. As exemplification of such acid-addition salts, there may be mentioned those of inorganic acids such as hydrochloric, hydrobromic, sulfuric and the like acids as well as those of organic acids such as acetic, maleic, fumaric, citric, succinic, oxalic, methanesulfonic and the like acids.

Excellent pharmacological activities represented by the compounds of the present invention are shown by the following experiments in comparison with those of Tolperisone which as previously mentioned has hitherto been clinically employed.

EXPERIMENTS (a) The compounds used for the tests:

(1) The compounds belonging to the present invention:

4'-ethyl-2-methyl-3-piperidino-propiophenone hydrochloride hereinafter-called "Compound A";

4'-n-propyl-2-methyl-3-piperidino-propiophenone hydrochloride hereinafter-called "Compound B"; and 4'-isopropyl-2-methyl-3-piperidino-propiophenone hydrochloride hereinafter-called "Compound C".

(2) The compounds used for control:

Tolperisone hydrochloride, i.e., 2,4'-dimethyl-3-piperidino-propiophenone hydrochloride hereinafter-called "Compound for control".

(b) Methods

Male d,d-strain mice weighing 18 to 22 grs. were used for the experiments.

Groups of each 10 mice were treated orally and intraperitoneally with a wide range of doses of the above-mentioned compounds or saline.

(1) Anti-tremorine activity:

Antagonistic effects on the tremorine-induced tremor were observed as follows:

Ten (10) minutes after the intraperitoneal injection of the individual compounds under test, on one hand, and 40 minutes after the oral administration of said individual compounds, on the other hand, 20 mg/kg of tremorine hydrochloride were subcutaneously injected to each group of the mice. The occurrence of tremor on the individually caged mice was visually observed 20 minutes after the tremorine-injection.

(2) Anti-nicotine and anti-physostigmine activities:

Antagonistic effects against the convulsive death of the mice caused by the injections of nicotine, on one hand, and physostigmine, on the other hand, were observed as follows:

Thirty (30) minutes after the intraperitoneal injection of the individual compounds under test, on one hand, and 60 minutes after the oral administration of said individual compounds, on the other hand, 4 mg/kg of nicotine tartrate, on one hand, and 0.5 mg/kg of physostigmine sulfate, on the other hand, were intravenously injected to each group of the mice. The convulsive death, if any, of the mice in each group was then observed.

(3) Other activities:

Following the oral administration of the individual compounds under test, changes in the gross behaviors of the mice were observed in particular with respect to the motor function and the maintenance of righting reflex.

The mortality ensued during 24 hours after the oral administration was recorded to determine acute toxicity of the compound under test on the mice.

Additionally, anti-histamine, anti-acetylcholine, anti-serotonin and smooth muscle-relaxing activities of the compounds under test were examined on isolated smooth muscle preparations (c) Results:

The numerals given in the following Table 1 indicate $ED_{50}$ values (in mg/kg) which were calculated 60 minutes after the oral administration of the compounds under test.

Table 1

|  | Compounds under Tests | | | Compound for Control |
| --- | --- | --- | --- | --- |
|  | A | B | C |  |
| Anti-tremorine activity | 32 | 50 | 118 | 210 |
| Anti-nicotine activity | 175 | 135 | 37 | 450 |
| Anti-Physostigmine activity | 84 | 150 | 50 | 400[1]< |
| Motor Ataxia | 640 | 800 | 84 | 800 |
| Acute toxicity (24 hours) | 800- | 1000- | 400- | 1000- |

Table 1-continued

|  | Compounds under Tests | | | Compound for Control |
| --- | --- | --- | --- | --- |
|  | A | B | C |  |
|  | 1000 | 1500 | 500 | 1500 |

[1]No effect up to the dose.

The numerals given in the following Table 2 indicate $ED_{50}$ values obtained from the result at the time of 30 minutes after the intraperitoneal injection of the individual compounds under test.

Table 2

|  | Compounds under test | | | Compound for Control |
| --- | --- | --- | --- | --- |
|  | A | B | C |  |
| Anti-tremorine activity | 23 | 21 | 25 | 80 |
| Anti-nicotine activity | 21 | 20 | 10 | 35 |

As is evident from the data given in the abovementioned Table 1, the acute toxicity of Compound B is almost equivalent to that of Compound under control. The acute toxicity of Compound A, on the other hand, is slightly stronger and the acute toxicity of Compound C is 2 to 3 times stronger than that of Compound under control.

Contrary to the above criticism on the toxicity, Compounds A, B and C, as is apparent from the data given in Tables 1 and 2, possess the pharmacological activities far stronger than those of Compound under control. More precisely, Compounds A, B and C were 2 to 7 times more potent than Compound under control on the anti-tremorine activity; 3 to 12 times more potent than Compound under control on the anti-nicotine activity; and 2 to 8 times more potent than Compound under control on the anti-physostigmine activity, all in the case of oral administration.

In like manner, Compounds A, B and C were 2 to 4 times more potent than Compound under control in the anti-tremorine and anti-nicotine activities, in the case of intraperitoneal administration.

In the further experiments on the isolated smooth muscle preparations, Compound under control produced a weak smooth muscle-relaxant activity in a potency of about $\frac{1}{3}$ times as compared with that exhibited by papaverine.

In contrast, it is notable, too, that Compound A with $4 \times 10^{-6}$ g/ml, Compound B with $10^{-6}$ g/ml and Compound C with $4 \times 10^{-7}$ g/ml in the respective concentrations that do not entirely produce anti-histamine and anti-acetylcholine activities, exhibited the strong smooth muscle-relaxant activities. The marked relaxant activities produced by Compounds A, B and C indeed are 2 to 3 times over the corresponding activity represented by papaverine and 3 to 10 times over the corresponding activity of Compound under control.

(d) Summary:

In viewpoint of the abovementioned pharmacological activities, it is obvious that the propiophenone derivatives specified in the present invention are superior to Compound under control, for example.

Accordingly, the specified propiophenone derivatives of the present invention are useful for the treatment of patients suffering from diseases such as muscular contracture, spastic paralysis, motor-disfunctions due to cerebral apoplexy, spinal and cerebral palsies, Parkinsonism and peripheral and cerebral vascular disorders, stiffness of shoulder due to hypertension and the like.

Following Examples will serve to illustrate the embodiments of the production of the compounds contemplated in the invention, but the invention, of course, is not intended to be limited thereby.

EXAMPLE 1

Preparation of 4'-ethyl-2-methyl-3-piperidino-propiophenone

To 60 mls. of isopropanol, there are introduced 120 grs. of 4-ethyl-propiophenone, 28.8 grs. of paraformaldehyde and 107 grs. of piperidine hydrochloride, and the resulting mixture is heated to reflux on an oil bath with stirring. The heating is continued, and when the reaction mixture solidifies, the state being a sign of completion of the reaction, there are added 500 mls. of acetone thereinto. The solidified mass is pulverized by crush, recovered by filtration and washed with acetone. 144 Grs. of the crude crystalline substance are thus obtained which are the hydrochloride of the purposed product. The hydrochloride is recrystallized from isopropanol, and there are obtained the crystalline needles having the melting point of 170°-172° C.

Elementary analysis of the product presumed as $C_{17}H_{25}NO.HCl$ gives:

|  | C | H | N |
| --- | --- | --- | --- |
| Calculated (%): | 69.00 | 8.87 | 4.73 |
| Found (%): | 68.99 | 8.92 | 4.59 |

EXAMPLE 2

Preparation of 4'-isopropyl-2-methyl-3-piperidino-propiophenone

To 350 mls. of isopropanol, there are introduced 350 grs. of 4-isopropyl-propiophenone, 270 grs. of a 30% aqueous formaldehyde and 266 grs. of piperidine hydrochloride together with 5 mls. of concentrated hydrochloric acid. The resulting mixture is heated to reflux on an oil bath with stirring for three hours. 500 mls. of acetone are then added to the reaction mixture with stirring. Crystals separate out from the reaction mixture are recovered by filtration and washed with acetone. There is thus obtained the crude hydrochloride of the purposed product in a crystalline form. The yield of the product amounts to 440 grs. The product is recrystallized from isopropanol and shows the melting point of 172°-174° C.

Elementary analysis of the product presumed as $C_{18}H_{27}NO.HCl$ gives:

|  | C | H | N |
| --- | --- | --- | --- |
| Calculated (%): | 69.75 | 9.12 | 4.52 |
| Found (%): | 69.86 | 9.21 | 4.29 |

EXAMPLE 3

A compound depicted in the following Table is prepared in accordance with the procedure disclosed in Example 1.

Table

| R | Molecular Formula (Melting Point) | Elementary Analysis Calculated (%) (Found) (%) | | |
| --- | --- | --- | --- | --- |
| | | C | H | N |
| —CH$_2$CH$_2$CH$_3$ | C$_{18}$H$_{27}$NO . HCl (168°–169° C.) | 69.75 (69.40) | 9.12 (9.21) | 4.52 (4.43) |

What is claimed is:

1. A 4'-Substituted 2-methyl-3-piperidino-propiophenone derivative represented by the formula:

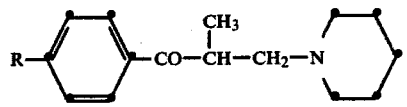

wherein R stands for a lower alkyl group having 2–3 carbon atoms or a pharmacologically acceptable acid-addition salt thereof.

2. A 4'-substituted-2-methyl-3-piperidino-propiophenone derivative according to claim 1 wherein the derivative is 4'-ethyl-2-methyl-3-piperidino-propiophenone or a pharmacologically acceptable acid-addition salt thereof.

3. A 4'-substituted-2-methyl-3-piperidino-propiophenone derivative according to claim 1 wherein the derivative is 4'-n-propyl-2-methyl-3-piperidino-propiophenone or a pharmacologically acceptable salt thereof.

4. A 4'-substituted-2-methyl-3-piperidino-propiophenone derivative according to claim 1 wherein the derivative is 4'-isopropyl-2-methyl-3-piperidino-propiophenone or a pharmacologically acceptable salt thereof.

* * * * *